United States Patent
Bahler et al.

(10) Patent No.: US 7,718,791 B2
(45) Date of Patent: May 18, 2010

(54) **SEPARATION OF CONTAMINANTS FROM *STREPTOCOCCUS PNEUMONIAE* POLYSACCHARIDE BY PH MANIPULATION**

(75) Inventors: Brian Bahler, Apex, NC (US); Tsu-shun Lee, Cary, NC (US); Jason Arnold Lotvin, Union, NJ (US); Mark Edward Ruppen, Garnerville, NY (US); Pamela Sue Fink Charbonneau, New City, NY (US)

(73) Assignee: Wyeth LLC, Madison, NJ (US)

( * ) Notice: Subject to any disclaimer, the term of this patent is extended or adjusted under 35 U.S.C. 154(b) by 185 days.

(21) Appl. No.: 11/396,108

(22) Filed: Mar. 31, 2006

(65) Prior Publication Data

US 2006/0228381 A1    Oct. 12, 2006

Related U.S. Application Data (60) Provisional application No. 60/669,546, filed on Apr. 8, 2005.

(51) Int. Cl.
   C07H 1/06    (2006.01)
   C07H 1/00    (2006.01)
   C12P 19/04    (2006.01)

(52) U.S. Cl. .................. 536/127; 536/123.1; 435/101

(58) Field of Classification Search ................. 435/101; 536/123.1; 514/54; 424/244.1, 831
   See application file for complete search history.

(56) References Cited

U.S. PATENT DOCUMENTS 5,714,354 A * 2/1998 Arnold et al. ............... 435/101

FOREIGN PATENT DOCUMENTS

| EP | 0002404 A | 6/1979 |
|----|-----------|--------|
| EP | 0024493 A2 | 3/1981 |
| EP | 0072513 A2 | 2/1983 |
| WO | WO 82/01995 A | 6/1982 |

OTHER PUBLICATIONS

Lee et al. Infect. Immun. 55: 1819-1823, 1987.*
Krishnamurthy et al. Infect. Immun. 22: 727-735, 1978.*
Ohno, N. et al; Microbiology and Immunology, 1982; vol. 26 (6); p. 523-530;Tokyo, JP.

* cited by examiner

*Primary Examiner*—S. Devi
(74) *Attorney, Agent, or Firm*—Joseph E. Zahner (57) ABSTRACT

A process for reducing the protein content and preserving the capsular polysaccharide content in a complex cellular *Streptococcus pneumoniae* lysate broth prior to purification is described. Utilizing pH reduction after cellular lysis has resulted in a purified polysaccharide that consistently meets the protein specification, and higher recovery yields of polysaccharide during the purification process.

14 Claims, 6 Drawing Sheets

SEPARATION OF CONTAMINANTS FROM *STREPTOCOCCUS PNEUMONIAE* POLYSACCHARIDE BY PH MANIPULATION

CROSS REFERENCE TO RELATED APPLICATION

This application is claims the benefit of U.S. Provisional Patent Application No. 60/669,546, filed Apr. 8, 2005.

BACKGROUND OF THE INVENTION

This invention relates to methods for removing excess soluble protein from cellular lysates of *Streptococcus pneumoniae* (*S. pneumoniae*) serotypes used in the production of pneumococcal polysaccharides.

The capsular polysaccharide for each *S. pneumoniae* serotype utilized for vaccine products is produced by growing the organism in a complex liquid medium. The population of the organism is often scaled up from a seed vial to seed bottles and passaged through one or more seed fermentors of increasing volume until production scale fermentation volumes are reached. The end of the growth cycle can be determined by one of several means, at which point the cells are lysed through the addition of a detergent which aids in the cell wall breakdown and release of autolysin which causes cellular lysis when the cells reach stationary phase. The lysate broth is then harvested for downstream (purification) processing. This purification includes several column chromatography and diafiltration steps to recover the capsular polysaccharide that surrounds the bacterial cells. The polysaccharide, when conjugated with a high molecular weight protein, such as $CRM_{197}$, and formulated into a vaccine containing conjugates of multiple serotypes, helps confer immunity (to *S. pneumoniae*) when injected into the target population, such as, for example, infants and young children.

Specifications have been set for the protein content in the purified polysaccharide of each serotype to reduce the risk of adverse events from the vaccine. For instance, in the currently marketed 7-valent pneumococcal conjugate (7vPnC) vaccine (Prevnar®), the specification for protein content in the purified serotype 4 polysaccharide is not more than 3%, and for the purified serotype 6B polysaccharide it is not more than 2% on a dry weight basis.

In some instances, it has proven difficult to remove the residual protein that is still present after the entire purification process. Efforts made to address this issue through changes in the purification processing of the cell lysate met with only moderate success.

It was therefore decided to attack this issue at the upstream side of the process. The key contaminant proteins were determined to be critical for cellular growth and integrity. Therefore, the remaining options available to reduce the total protein consisted of altering growth and/or harvest conditions.

The fermentation process is fairly straightforward. The cells (seed) are expanded in bottles of soy-based media, then passed through one or two seed fermentors, and finally passaged to a production scale fermentor. At each step the temperature and pH are closely monitored with pH being controlled by the addition of a base material (20% sodium carbonate). When the growth reaches a certain point, the run is ended by the introduction of a detergent, such as deoxycholate (DOC) sodium, which initiates a cell lysis process. After a hold period, the pH of the lysate broth is adjusted to 6.6 to precipitate the deoxycholate and cell membrane complexes. This material is held until processing by centrifugation and filtration can be carried out to remove the solids.

Much of the protein, however, remains solubilized in the clarified lysate, causing the residual protein content in the purified polysaccharide to exceed specification. Thus, there is a need to reduce the soluble protein levels in several pneumococcal serotypes during either the fermentation or purification process.

SUMMARY OF THE INVENTION

The present invention fulfills this need by providing a process for reducing the protein content and preserving the capsular polysaccharide content in a complex cellular *Streptococcus pneumoniae* lysate broth prior to purification. This process comprises the steps of:

(a) growing a selected *S. pneumoniae* serotype in a soy-based medium, which includes:
  (i) inoculating a first container containing the soy-based medium with seed stock of the selected serotype, and incubating the first container until growth requirements are met, and
  (ii) inoculating a second container containing the soy-based medium with the culture from step (i) while maintaining a stable pH and temperature in the second container, and
(b) lysing with a detergent the bacterial cells produced in step (a), thereby producing a lysate containing soluble proteins, cell debris, nucleic acids and polysaccharide;
(c) agitating the cellular lysate for a time sufficient to assure complete lysis and polysaccharide release;
(d) lowering the pH of the cellular lysate to less than 5.5 to precipitate out the detergent and most of the soluble proteins;
(e) holding the solution and precipitate formed in step (d) without agitation for a time sufficient to allow settling of the precipitate; and
(f) processing the solution and precipitate by centrifugation and/or filtration, whereby the capsular polysaccharide in solution is preserved and the soluble protein is effectively reduced.

Exemplary, non-limiting *S. pneumoniae* serotypes selected for this embodiment of the invention are 1, 4, 5, 6A, 6B, 7F and 19A. In a particular embodiment of the invention, and depending on the serotype being grown in step (a), the fermentation pH in step (a) is maintained by a base feed of sodium hydroxide, sodium carbonate, or a combination thereof. In another embodiment, the pH in step (d) is lowered to between 4.5 and less than 5.5. In yet another embodiment, the detergent is deoxycholate sodium.

This invention also relates to a process for reducing the protein content and preserving the capsular polysaccharide content in a complex cellular *Streptococcus pneumoniae* lysate broth prior to purification. The process comprises the steps of:

(a) expanding in increasing volumes from a starting container to a production scale container in a soy-based medium a selected *S. pneumoniae* serotype and maintaining a stable pH and temperature during cellular growth;
(b) lysing with a detergent the bacterial cells produced in step (a), thereby producing a lysate containing soluble proteins, cell debris, nucleic acids and polysaccharide;
(c) agitating the cellular lysate for a time sufficient to assure complete lysis and polysaccharide release;
(d) lowering the pH of the cellular lysate to less than 5.5 to precipitate out the detergent and most of the soluble proteins;

(e) holding the solution and precipitate formed in step (d) without agitation for a time sufficient to allow settling of the precipitate; and
(f) processing the solution and precipitate by centrifugation and/or filtration, whereby the capsular polysaccharide in solution is preserved and the soluble protein is effectively reduced.

Exemplary, non-limiting *S. pneumoniae* serotypes selected for this embodiment of the invention are 1, 4, 5, 6A, 6B, 7F and 19A. In a particular embodiment of the invention, and depending on the serotype being grown in step (a), the fermentation pH in step (a) is maintained by a base feed of sodium hydroxide, sodium carbonate, or a combination thereof. In another embodiment, the pH in step (d) is lowered to between 4.5 and less than 5.5. In still another embodiment, the detergent is deoxycholate sodium.

In yet another embodiment, where the serotype is serotype 5 or 19A, the soy-based medium is supplemented with sodium bicarbonate.

This invention allows for removal of large quantities of excess protein contamination from the cellular lysate, thereby leaving a cleaner product (Cell Free Broth or CFB) for purification which will generally obtain higher polysaccharide recoveries and total polysaccharide yields than were possible using prior fermentation and recovery method.

DETAILED DESCRIPTION OF THE INVENTION

*Streptococcus pneumoniae* are Gram-positive, lancet shaped cocci that are usually seen in pairs (diplococci), but also in short chains or as single cells. They grow readily on blood agar plates with glistening colonies and display alpha hemolysis unless grown anaerobically where they show beta hemolysis. They are sensitive to bile salts that can break down the cell wall with the presence of the cells' own enzyme, autolysin. The organism is an aerotolerant anaerobe and is fastidious in that it has complex nutritional requirements.

The cells of most pneumococcal serotypes have a capsule which is a polysaccharide coating surrounding each cell. This capsule is a determinant of virulence in humans because it interferes with phagocytosis by preventing antibodies from attaching to the bacterial cells. There are currently 90 capsular serotypes identified, with 23 serotypes responsible for about 90% of invasive disease. The polysaccharide coat as a vaccine can confer a reasonable degree of immunity (to *S. pneumoniae*) in individuals with developed or unimpaired immune systems, but a conjugated protein with polysaccharide allows for an immune response in infants and elderly who are also most at risk for pneumococcal infections. It is important to be able to separate this capsular polysaccharide from the lysed (killed) bacteria and remove as much cellular debris as possible. As described herein, this removal was accomplished in a series of fermentation process changes.

Three major changes that have greatly improved the downstream processing are as follows: (1) changing the fermentation base feed from sodium carbonate to sodium hydroxide where possible; (2) maintaining agitation in the fermentor during the deoxycholate hold interval; and (3) lowering the pH after the deoxycholate lysate hold to less than 5.5.

The initial discovery was that by lowering the pH to less than 5.5, from 50-90% of the undesirable soluble protein could be removed from the cell lysate prior to downstream processing (purification). While this was a very important process enhancement, the use of large volumes of sodium carbonate to maintain the set-point pH during the fermentation runs caused a serious foaming problem when the pH was adjusted to 5.0 with acetic acid. It was also discovered that a stable pH was difficult to maintain after adjustment because of the multiple forms of carbonate that exist in solution. This led to looking at alternate base feeds that would not create a carbonate buildup in the fermentation broth. Sodium hydroxide was selected because it was already being used to adjust the pH of the medium and seed bottles prior to inoculation. Studies up to 100L fermentations indicated that this was a viable alternative with only a minor reduction in growth, based on optical density (OD). This base also resolved the foaming problem. Other bases besides sodium hydroxide can be used, and sodium bicarbonate can be used as a supplement where it is determined that the organism requires some form of carbonate to maintain growth, such as, for example, with serotypes 5 and 19A. If sodium carbonate is used as the primary base feed, such as for serotype 19A, then the post-lysate pH adjustment (to a pH of less than 5.5) requires a slow multi-hour controlled acid addition to avoid foaming.

Finally, based on laboratory observation, it was determined that if the deoxycholate hold proceeded without agitation (as in a previous protocol), a gel-like precipitate would settle on the fermentor walls and pH probe. This created unreliable in-situ pH readings when the pH was adjusted. The agitation step prevented this precipitate from forming and allowed the pH probe integrity to be maintained.

Thus, in the presently claimed invention, the selected *Streptococcus pneumoniae* serotypes are expanded in increasing volumes from starting seed vials in a sterile medium composed of, for example, an enzyme digested soy-based product, sodium chloride, potassium phosphate monobasic, calcium chloride, and a selected amino acid. Dextrose with magnesium sulfate is used as the carbon source to sustain growth in the liquid medium. The medium may also be supplemented with other additives as required by the specific serotype or process. The culture starts in a first container, such as seed bottles, which, after a growth interval in a convection-based incubator, is used to inoculate a second container, such as a seed fermentor, which in turn can be used to inoculate, if desired, at least one progressively larger container, such as a production fermentor, until production scale is reached. In one embodiment, a selected S. pneumoniae serotype is expanded in increasing volumes from starting seed vials to seed bottles to a 20L fermentor to a 200L fermentor to a 2000L production fermentor. The growth parameters are closely monitored for optical density, temperature and pH in order to determine when to transfer the culture to the next fermentation scale and also when to terminate the batch run.

When the bacteria enter stationary phase, the cells in the production fermentor are forced into lysis by the addition of a detergent, such as an anionic or cationic detergent. Representative examples of such detergents include deoxycholate sodium, N-lauryl sarcosine, chenodeoxycholic acid sodium, and saponins. After agitating the cellular lysate for a time sufficient to assure complete cellular death, e.g., for a time between 8 and 24 hours and a temperature between 7° C. and 13° C., the second phase of the process is to reduce the pH of the cellular lysate to less than pH 5.5 with an acid solution, such as 50% acetic acid. The actual pH reduction varies by serotype with the purpose of being able to be below the final purified protein specification on a consistent basis required for a robust production process. In a particular embodiment of the invention, the pH is lowered to between 4.5 and less than 5.5.

The pH reduction step causes a "salting out" (precipitation) of formerly soluble proteins. This is a well-known chemical effect on proteins as they reach their isoelectric points. What makes this step unique in the present invention is that it is being used as a purification step in a highly complex cellular lysate broth. The broth is defined as "complex" because it contains medium components, DNA, proteins, polysaccharides, RNA, and other cellular debris.

In addition to acetic acid, the claimed process has also been shown to work with sulfuric and phosphoric acids, and should work with varying efficiencies following the Hofmeister series of which these acids are a part. The Hofmeister series is the ranking of various anions and cations and their ability to precipitate out mixtures of proteins. The final concentration of these compounds (in the Hofmeister series) in solution determines the ultimate solubility of the various proteins.

After a hold time, without agitation, that is sufficient to allow settling of the precipitate and thereby aid the continuous centrifugation process, such as, for example, between 12 and 24 hours at a temperature between 15° C. and 25° C., a significant portion of the previously soluble proteins (and likely some of the other previously soluble contaminant components) drop out of solution as a solid precipitate with little loss or degradation of the polysaccharide product which remains in solution.

This solution with the precipitate is then processed through a continuous centrifuge or alternately by standard bottle centrifugation. The supernatant that contains the polysaccharide is collected and run through particulate and micron filtration prior to being transferred for downstream concentration and purification.

Figure 1:
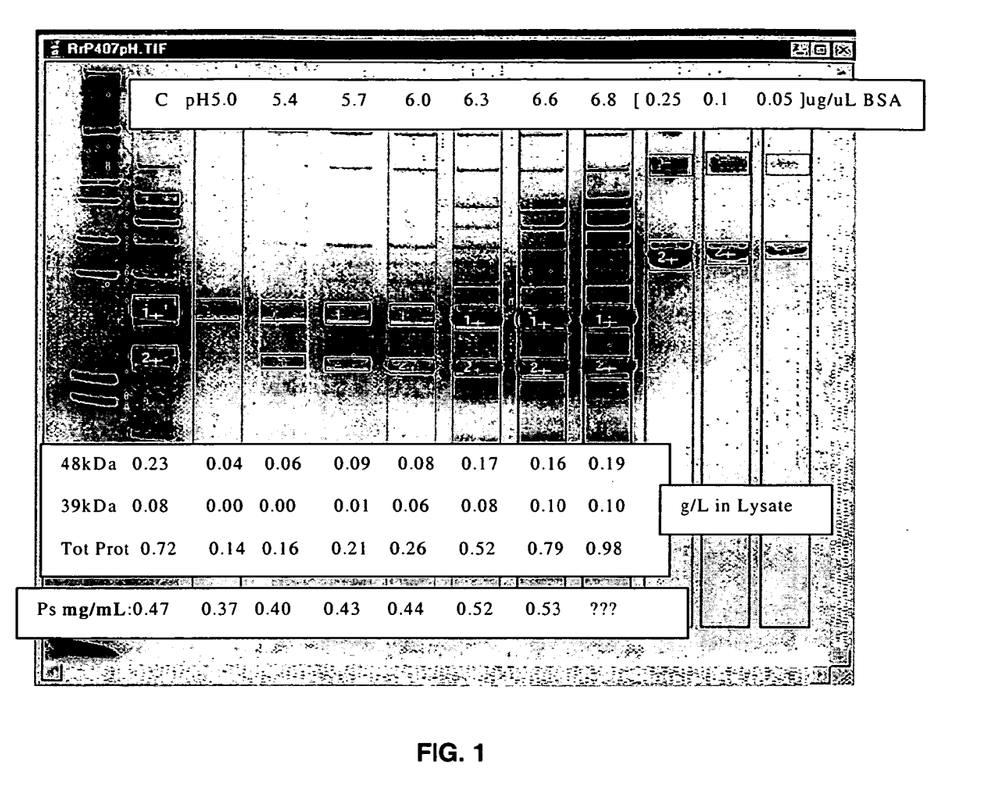
FIG. 1 is an SDS-PAGE gel showing the significant decrease in soluble protein in grams per liter of lysate as the pH is decreased with acetic acid for *S. pneumoniae* Type 4. The 39 kDa and 48 kDa components are cell wall surface proteins. The polysaccharide yield is also shown.

Results of using the process of this invention are depicted in the Figures. FIG. 1 shows a representative SDS-PAGE gel of the observed protein reduction using acetic acid to reduce the pH from 6.8 to 5.0 on the cellular lysate broth for S. pneumoniae serotype 4. The far left lane is a molecular weight marker used as a reference for protein weight. Sample Lane 1 ("C") is a control that was not pH adjusted. The numbers show the approximate value (g/L in lysed broth) of the two major protein contaminant bands (48 kDa and 39 kDa) and also the total protein in the whole lane. Also shown is the total polysaccharide yield contained in a sample aliquot submitted for HPLC-SEC analysis. Lanes 2-8 show the same information from the pH adjusted samples. Lanes 9-11 are BSA standards used to determine the protein yields by basic linear regression analysis. The Ps analysis was not done on the pH 6.8 sample. In this particular serotype, there was some moderate loss of polysaccharide (Ps) but at a much lower rate than the loss of protein through reduction of pH.

Figure 2:
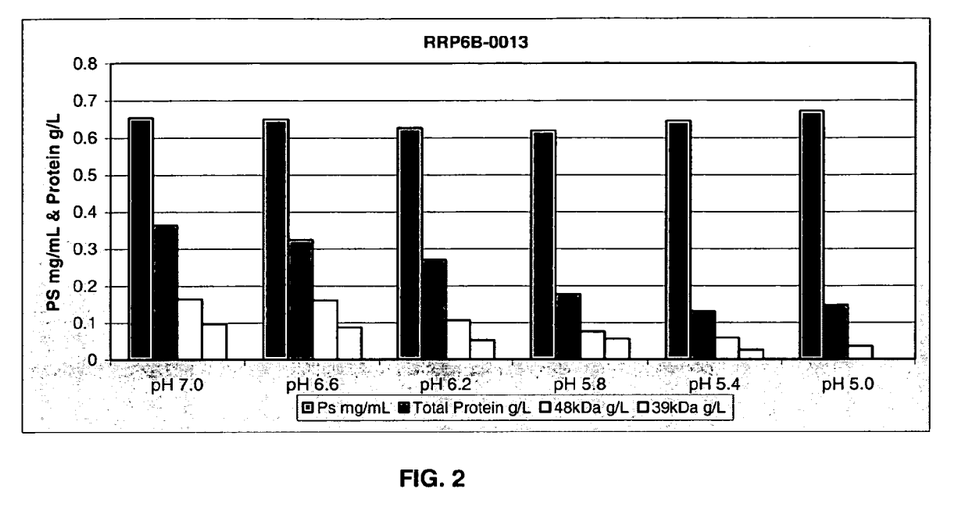
FIG. 2 is a chart of results for *S. pneumoniae* Type 6B of pH adjustment down to pH 5 showing protein reduction as determined by SDS-PAGE and polysaccharide (Ps) yield as determined by HPLC-SEC with refractive index (RI) detector.

FIG. 2 is a plotted graph illustrating the protein reduction in the cellular lysate of S. pneumoniae serotype 6B along with the polysaccharide yield stability when the pH of the cellular lysate was lowered to 5.0. No loss of polysaccharide was seen with this serotype. In contrast, total protein was reduced by more than one-half.

Figure 3:
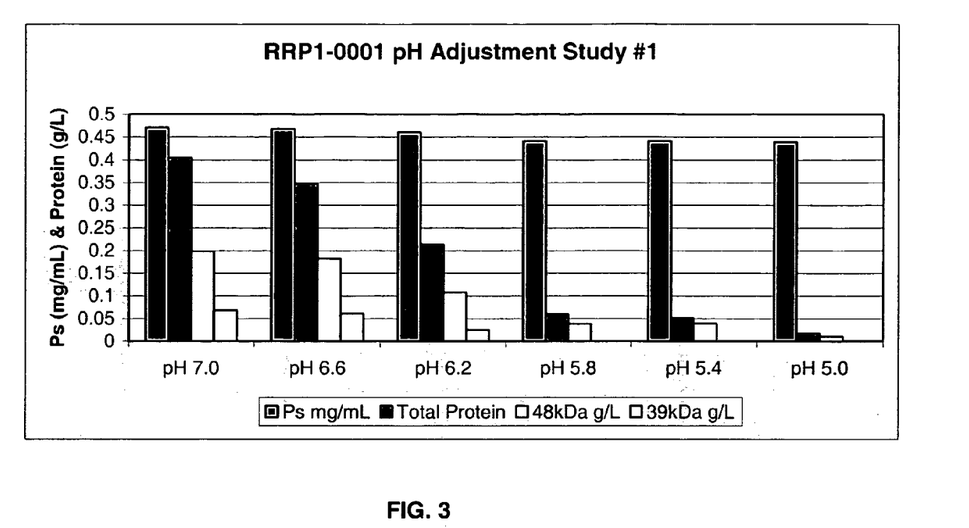
FIG. 3 is a chart of results for *S. pneumoniae* Type 1 of pH adjustment down to pH 5 showing protein reduction as determined by SDS-PAGE and polysaccharide yield as determined by HPLC-SEC with RI detector.

FIG. 3 is a plotted graph illustrating the protein reduction in the cellular lysate of S. pneumoniae serotype 1 along with the polysaccharide yield stability when the pH of the cellular lysate was lowered to 5.0. Almost no change in polysaccharide concentration was observed. In contrast, total protein was reduced by more than 90%.

Figure 4:
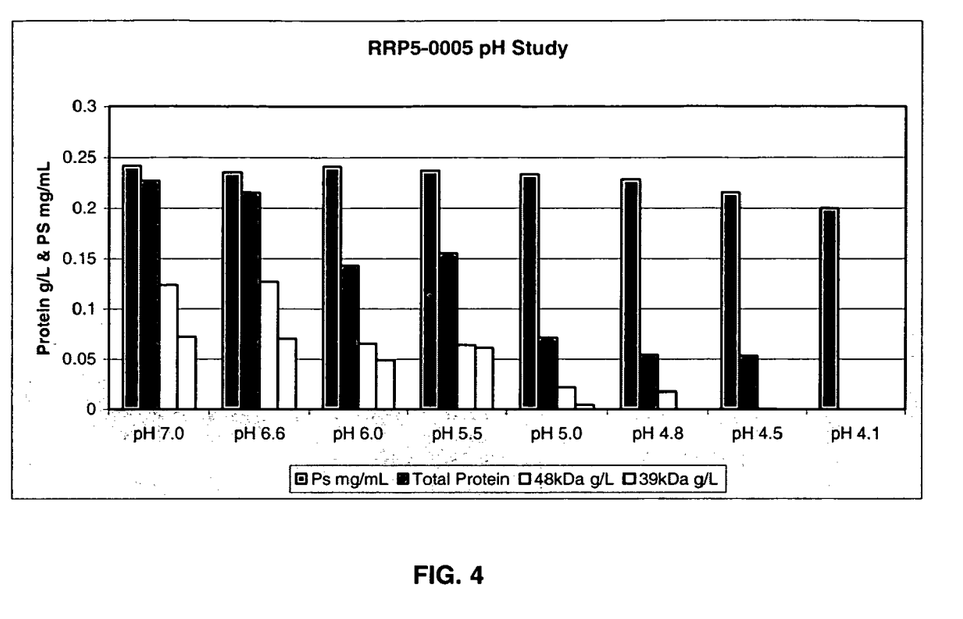
FIG. 4 is a chart of results for *S. pneumoniae* Type 5 of pH adjustment down to pH 4.1 showing protein reduction as determined by SDS-PAGE and polysaccharide yield as determined by HPLC-SEC with RI detector.

FIG. 4 is a plotted graph illustrating the protein reduction in the cellular lysate of S. pneumoniae serotype 5 along with the polysaccharide yield stability when the pH of the cellular lysate was lowered to 4.1. Almost no change in polysaccharide concentration was observed until very low pH, which was attributed to a dilution effect due to the amount of acid added. In contrast, total protein was reduced by more than 75% at pH 4.5.

Figure 5:
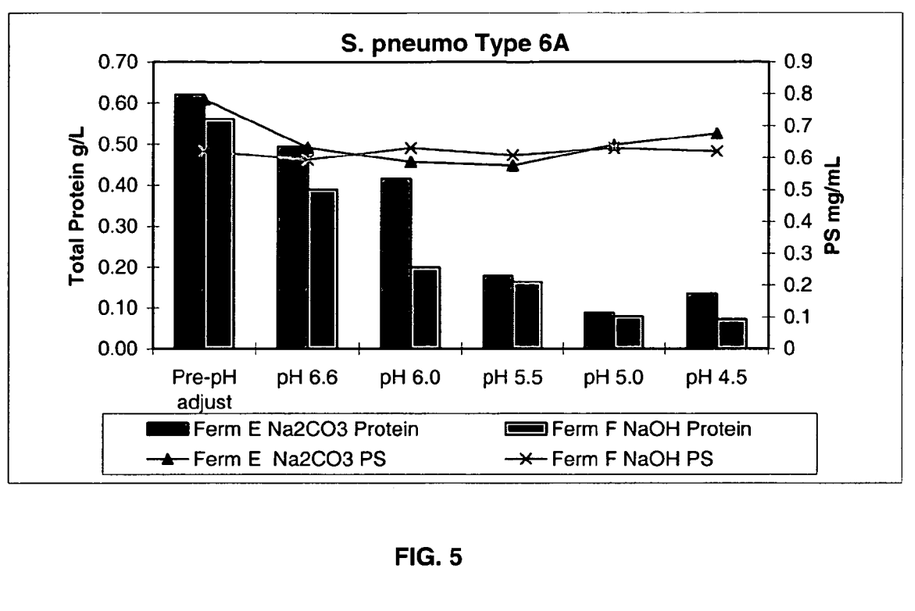
FIG. 5 is a chart of results for *S. pneumoniae* Type 6A of pH adjustment down to pH 4.5 of two different fermentation runs showing protein reduction as determined by SDS-PAGE and polysaccharide yield as determined by HPLC-SEC with RI detector.

FIG. 5 is a plotted graph of two different fermentation runs illustrating the protein reduction in the cellular lysate of S. pneumoniae serotype 6A along with the polysaccharide yield stability when the pH of the cellular lysate was lowered to 4.5. Almost no change in polysaccharide concentration was observed. This graph also shows that polysaccharide concentrations were maintained while protein concentrations were reduced when NaOH was used instead of $Na_2CO_3$.

Figure 6:
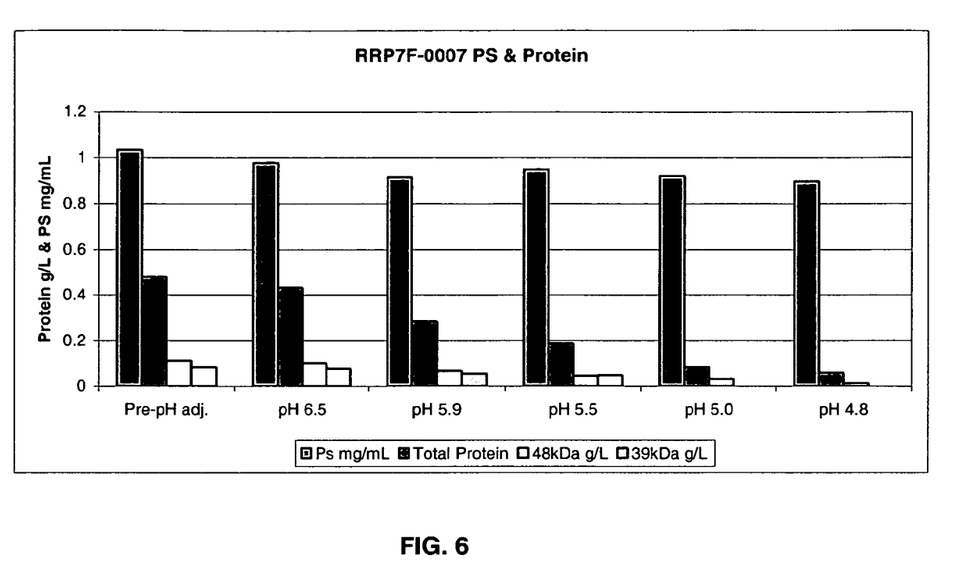
FIG. 6 is a chart of results for *S. pneumoniae* Type 7F of pH adjustment down to pH 4.8 showing protein reduction as determined by SDS-PAGE and polysaccharide yield as determined by HPLC-SEC with RI detector.

FIG. 6 is a plotted graph illustrating the protein reduction in the cellular lysate of S. pneumoniae serotype 7F along with the polysaccharide yield stability when the pH of the cellular lysate was lowered to 4.8. Almost no change in polysaccharide concentration was observed. In contrast, total protein was reduced by more than 80% at pH 4.8.

Table 1 below is representative of some of the protein reduction and polysaccharide gains from final purified polysaccharides after the process of this invention was utilized.

TABLE 1

Protein Concentration and Polysaccharide Yield for Several S. pneumoniae Serotypes

| | | Original Process | | Process of the Invention | |
|---|---|---|---|---|---|
| Serotype | Protein Specification | Protein Conc. | Ps Yield | Protein Conc. | Ps Yield |
| 1 | ≦2.0% | 11.7% | 11.2 g | <0.8% | 15~20 g |
| 5 | ≦7.5% | 10.2% | 6.0 g | <6.5%* | 8~13 g |
| 7F | ≦5.0% | 0.2% | 19.2 g | 0.2% | 53 g |
| 6A | ≦2.0% | NA | NA | 0.3% | 21.6 g |

*Fermentation process showed an 80% protein reduction of DOC lysate material but additional protein removal was not as efficient during purification process.

The fermentation process changes outlined above served to greatly reduce the protein content of the lysate broth prior to purification processing. This has allowed the purified product to meet the protein specification without significant modification of the current purification process for polysaccharide recovery. An unexpected benefit of these changes was a total purification polysaccharide yield improvement of 25-100% despite slightly lower growth as determined by OD. This is a robust improvement of the fermentation/recovery process that can greatly enhance the production of pneumococcal polysaccharides.

The above disclosure generally describes the present invention. A more complete understanding can be obtained by reference to the following specific examples. These examples are described solely for the purpose of illustration and are not intended to limit the scope of the invention.

EXAMPLES

Example 1

Protein Reduction in the Cellular Lysate of S. pneumoniae Serotypes 1, 6A and 7F Preparation of Master and Working Cell Banks S. pneumoniae serotype 1 was obtained from the American Type Culture Collection, ATCC, strain 6301. S. pneumoniae serotypes 6A and 7F were obtained from Dr. Gerald Shiffman of the State University of New York. Several generations of seed stocks were created in order to expand the strain and remove components of animal origin (generations F1, F2, and F3). Two additional generations of seed stocks were produced. The first additional generation was made from an F3 vial, and the subsequent generation was made from a vial of the first additional generation. Seed vials were stored frozen (<−70° C.) with synthetic glycerol as a cryopreservative. In addition to frozen vials, lyophilized vials were prepared for the F4 generation. For cell bank preparation, all cultures were grown in a soy-based medium. Prior to freezing, cells were concentrated by centrifugation, spent medium was removed, and cell pellets were re-suspended in fresh medium containing a cryopreservative, such as synthetic glycerol.

Fermentation and Recovery

Cultures from the working cell bank were used to inoculate seed bottles containing a soy-based medium (Table 2). The bottles were incubated at 36° C.±2° C. without agitation until growth requirements were met. A seed bottle was used to inoculate a seed fermentor containing the soy-based medium. A pH of about 7 was maintained with 3N NaOH. After the target optical density was reached, the seed fermentor was used to inoculate the production fermentor containing the soy-based medium. The pH was maintained with 3N NaOH. The fermentation was terminated after cessation of growth or when the working volume of the fermentor was reached. An appropriate amount of sterile 12% deoxycholate sodium was added to the culture to obtain a 0.12%-0.13% concentration in the broth, to lyse the bacterial cells and release cell-associated polysaccharide. After lysing, the fermentor contents were agitated for a time interval between 8 and 24 hours at a temperature between 7° C. and 13° C., to assure that complete cellular lysis and polysaccharide release had occurred. Agitation during this hold period prevented lysate sediment from settling on the fermentor walls and pH probe, thereby allowing the pH probe integrity to be maintained. Next, the pH of the lysed culture broth was adjusted to approximately pH 5.0 with 50% acetic acid. After a hold time without agitation, for a time interval between 12 and 24 hours at a temperature between 15° C. and 25° C., a significant portion of the previously soluble proteins dropped out of solution as a solid precipitate with little loss or degradation of the polysaccharide, which remained in solution. The solution with the precipitate was then clarified by continuous flow centrifugation followed by depth filtration and 0.45 µm microfiltration.

On a smaller scale, the process described above also resulted in significant reduction of total protein for serotypes 4 and 6B (FIGS. 1 and 2), which indicates that the process will work for these two serotypes on a larger scale. (S. pneumoniae serotypes 4 and 6B were also obtained from Dr. Gerald Shiffman of the State University of New York.)

TABLE 2

Composition of Soy-Based Medium

| Component | Baseline Concentration | Low Concentration | High Concentration |
|---|---|---|---|
| HySoy | 28 g/L | 18 g/L | 38 g/L |
| NaCl | 3.5 g/L | 3.5 g/L | 3.5 g/L |
| KH$_2$PO$_4$ | 0.7 g/L | 0.7 g/L | 0.7 g/L |
| CaCl$_2$—H$_2$O | 0.018 g/L | 0.018 g/L | 0.018 g/L |
| L-Cysteine, HCl | 0.21 g/L | 0.21 g/L | 0.21 g/L |

Example 2

Protein Reduction in the Cellular Lysate of S. pneumoniae Serotype 5

S. pneumoniae serotype 5 was obtained from Dr. Gerald Schiffman of the State University of New York, Brooklyn, N.Y. For preparation of the cell bank system, see Example 1.

Fermentation and Recovery

Cultures from the working cell bank were used to inoculate seed bottles containing the soy-based medium described above (Table 2), which medium was supplemented with a sterile NaHCO$_3$ solution at a 10 mM concentration. The bottles were incubated at 36° C.±2° C. without agitation until growth requirements were met. A seed bottle was used to inoculate a seed fermentor containing the soy-based medium with a 10 mM NaHCO$_3$ concentration in the medium. A pH of about 7.0 was maintained with 3N NaOH. After the target optical density was reached, the seed fermentor was used to inoculate the production fermentor containing the soy-based medium with a 10 mM NaHCO$_3$ concentration in the medium. The pH was maintained with 3N NaOH. The fermentation was terminated after cessation of growth or when the working volume of the fermentor was reached. An appropriate amount of sterile 12% deoxycholate sodium was added to the culture to obtain a 0.12%-0.13% concentration in the broth, to lyse the bacterial cells and release cell-associated polysaccharide. After lysing, the fermentor contents were agitated for a time interval between 8 and 24 hours at a temperature between 7° C. and 13° C. to assure that complete cellular lysis and polysaccharide release had occurred. Agitation during this hold period prevented lysate sediment from settling on the fermentor walls and pH probe, thereby allowing the pH probe integrity to be maintained. Next, the pH of the lysed culture broth was adjusted to approximately pH 4.8 with 50% acetic acid. After a hold time without agitation, for a time interval between 12 and 24 hours at a temperature between 15° C. and 25° C., a significant portion of the previously soluble proteins dropped out of solution as a solid precipitate with little loss or degradation of the polysaccharide, which remained in solution. The solution with the precipitate was then clarified by continuous flow centrifugation followed by depth filtration and 0.45 µm microfiltration.

It should be understood that the foregoing discussion and examples merely present a detailed description of certain embodiments. It therefore should be apparent to those of ordinary skill in the art that various modifications and equivalents can be made without departing from the spirit and scope of the invention.

What is claimed is:

1. A process of reducing the protein content and preserving the capsular polysaccharide content in a complex cellular *Streptococcus pneumoniae* lysate broth, the process comprising the steps of:
   (a) growing bacterial cells of a selected *S. pneumoniae* serotype in a soy-based medium, which includes:
      (i) inoculating a first container containing the soy-based medium with seed stock of the selected serotype, and incubating the first container until growth requirements are met,
      (ii) inoculating a second container containing the soy-based medium with the culture from step (i) while maintaining a stable pH and temperature in the second container, and
   (b) lysing with a detergent the bacterial cells produced in step (a), thereby producing a cellular lysate containing soluble proteins, cell debris, nucleic acids and polysaccharide;
   (c) agitating the cellular lysate for a time sufficient to assure complete lysis and capsular polysaccharide release;
   (d) lowering the pH of the cellular lysate to between 4.5 and less than 5.5 to precipitate out the detergent and most of the soluble proteins, thereby producing a solution and a precipitate;
   (e) holding the solution and the precipitate formed in step (d) without agitation for a time sufficient to allow settling of the precipitate; and
   (f) processing the solution and the precipitate by centrifugation and/or filtration, whereby the capsular polysaccharide is preserved and the soluble protein is effectively reduced.

2. The process of claim 1, wherein the selected *S. pneumoniae* serotype is 1, 4, 5, 6A, 6B, 7F or 19A.

3. The process of claim 1, wherein the detergent is deoxycholate sodium.

4. The process of claim 1, wherein the pH in step (a) is maintained by a base feed of sodium hydroxide, sodium carbonate, or a combination thereof.

5. A process of reducing the protein content and preserving the capsular polysaccharide content in a complex cellular *Streptococcus pneumoniae* lysate broth, the process comprising the steps of:
   (a) expanding in increasing volumes from a staffing container to a production scale container in a soy-based medium bacterial cells of a selected *S. pneumoniae* serotype and maintaining a stable pH and temperature during cellular growth;
   (b) lysing with a detergent the bacterial cells produced in step (a), thereby producing a cellular lysate containing soluble proteins, cell debris, nucleic acids and polysaccharide;
   (c) agitating the cellular lysate for a time sufficient to assure complete lysis and capsular polysaccharide release;
   (d) lowering the pH of the cellular lysate to between 4.5 and less than 5.5 to precipitate out the detergent and most of the soluble proteins, thereby producing a solution and a precipitate;
   (e) holding the solution and the precipitate formed in step (d) without agitation for a time sufficient to allow settling of the precipitate; and
   (f) processing the solution and the precipitate by centrifugation and/or filtration, whereby the capsular polysaccharide is preserved and the soluble protein is effectively reduced.

6. The process of claim 5, wherein the selected *S. pneumoniae* serotype is 1, 4, 5, 6A, 6B, 7F or 19A.

7. The process of claim 5, wherein the detergent is deoxycholate sodium.

8. The process of claim 5, wherein the pH in step (a) is maintained by a base feed of sodium hydroxide, sodium carbonate, or a combination thereof.

9. A process of reducing the protein content and preserving the capsular polysaccharide content in a complex cellular *Streptococcus pneumoniae* lysate broth, the process comprising the steps of:
   (a) expanding in increasing volumes from a staffing container to a production scale container in a soy-based medium bacterial cells of a selected *S. pneumoniae* serotype selected from the group consisting of serotypes 1, 4, 6A, 6B and 7F, and maintaining a stable pH and temperature during cellular growth, the pH being maintained with sodium hydroxide;
   (b) lysing with a detergent the bacterial cells produced in step (a), thereby producing a cellular lysate containing soluble proteins, cell debris, nucleic acids and polysaccharide;
   (c) agitating the cellular lysate for a time sufficient to assure complete lysis and capsular polysaccharide release;
   (d) lowering the pH of the cellular lysate to between 4.5 and less than 5.5 to precipitate out the detergent and most of the soluble proteins, thereby producing a solution and a precipitate;
   (e) holding the solution and the precipitate formed in step (d) without agitation for a time sufficient to allow settling of the precipitate; and
   (f) processing the solution and the precipitate by centrifugation and/or filtration, whereby the capsular polysaccharide is preserved and the soluble protein is effectively reduced.

10. The process of claim 9, wherein the detergent is deoxycholate sodium.

11. A process of reducing the protein content and preserving the capsular polysaccharide content in a complex cellular *Streptococcus pneumoniae* lysate broth, the process comprising the steps of:
   (a) expanding in increasing volumes bacterial cells of *S. pneumoniae* serotype 5, from a starting container to a production scale container in a soy-based medium supplemented with sodium bicarbonate, and maintaining a stable pH and temperature during cellular growth, the pH being maintained with sodium hydroxide;
   (b) lysing with a detergent the bacterial cells produced in step (a), thereby producing a cellular lysate containing soluble proteins, cell debris, nucleic acids and polysaccharide;
   (c) agitating the cellular lysate for a time sufficient to assure complete lysis and capsular polysaccharide release;

(d) lowering the pH of the cellular lysate to between 4.5 and less than 5.5 to precipitate out the detergent and most of the soluble proteins, thereby producing a solution and a precipitate;

(e) holding the solution and the precipitate formed in step (d) without agitation for a time sufficient to allow settling of the precipitate; and (f) processing the solution and the precipitate by centrifugation and/or filtration, whereby the capsular polysaccharide is preserved and the soluble protein is effectively reduced.

12. The process of claim 11, wherein the detergent is deoxycholate sodium.

13. A process of reducing the protein content and preserving the capsular polysaccharide content in a complex cellular *Streptococcus pneumoniae* lysate broth, the process comprising the steps of:

(a) expanding in increasing volumes bacterial cells of *S. pneumoniae* serotype 19A, from a starting container to a production scale container in a soy-based medium supplemented with sodium bicarbonate, and maintaining a stable pH and temperature during cellular growth, the pH being maintained with sodium carbonate;

(b) lysing with a detergent the bacterial cells produced in step (a), thereby producing a cellular lysate containing soluble proteins, cell debris, nucleic acids and polysaccharide;

(c) agitating the cellular lysate for a time sufficient to assure complete lysis and capsular polysaccharide release;

(d) lowering the pH of the cellular lysate to between 4.5 and less than 5.5 to precipitate out the detergent and most of the soluble proteins, thereby producing a solution and a precipitate;

(e) holding the solution and the precipitate formed in step (d) without agitation for a time sufficient to allow settling of the precipitate; and (f) processing the solution and the precipitate by centrifugation and/or filtration, whereby the capsular polysaccharide is preserved and the soluble protein is effectively reduced.

14. The process of claim 13, wherein the detergent is deoxycholate sodium.

* * * * *